(12) United States Patent
Kim et al.

(10) Patent No.: US 8,333,998 B2
(45) Date of Patent: Dec. 18, 2012

(54) HERBAL MIXTURE EXTRACT OF REHMANNIAE RADIX PREPARATA AND ACANTHOPANACIS CORTEX AND A COMPOSITION COMPRISING THE SAME FOR PREVENTION AND TREATMENT OF OSTEOPOROSIS

(75) Inventors: Jung-Keun Kim, Seongnam-si (KR); Se-Won Kim, Cheonan-si (KR); Hyung-Gun Kim, Seoul (KR); Seon-Yle Ko, Daejeon (KR); Dong-Heon Baek, Seoul (KR)

(73) Assignee: Oscotec Inc., Cheonan-si, Chungeheongnam-do (KR)

( * ) Notice: Subject to any disclaimer, the term of this patent is extended or adjusted under 35 U.S.C. 154(b) by 258 days.

(21) Appl. No.: 12/133,626

(22) Filed: Jun. 5, 2008

(65) Prior Publication Data

US 2008/0254151 A1 Oct. 16, 2008

Related U.S. Application Data

(60) Division of application No. 11/844,237, filed on Aug. 23, 2007, now Pat. No. 8,053,001, which is a continuation of application No. PCT/KR2006/000634, filed on Feb. 23, 2006.

(30) Foreign Application Priority Data

Feb. 23, 2005 (KR) .......................... 10-2005-0015049

(51) Int. Cl.
*A61K 36/00* (2006.01)
*A61K 36/254* (2006.01)

(52) U.S. Cl. ...................................... 424/725; 424/728

(58) Field of Classification Search .................. None
See application file for complete search history.

(56) References Cited

U.S. PATENT DOCUMENTS 6,312,467 B1 * 11/2001 McGee ...................... 623/16.11

FOREIGN PATENT DOCUMENTS

| KR | 2003-718430 | * | 7/2001 |
| KR | 2002-737882 | * | 6/2002 |
| KR | 2003034825 A | * | 5/2003 |

OTHER PUBLICATIONS

Kim et al. (Effects of Herbal Medicine on Tibia Bone Changes in Ovariectomized Rats and Sam P6 Mice, Yahhak Hoeji vol. 42 pp. 220-228, 1998).*
Herbal Combinations for Illiness (website http://web.archive.org/web/20030210135948/http:/www.naturalark.com/herbcomb.html, copyrighted 1996-2003).*
Kim, et al., "OPB, a water extract from Rehmanniae Radix glutinose Libosch and Eleutherococcus senticosus Maz inhibits osteoclast differentiation and function", International Journal of Oral Biology, vol. 32, No. 1, Mar. 31, 2007, pp. 23-34.

* cited by examiner

*Primary Examiner* — Terry McKelvey
*Assistant Examiner* — Randall Winston
(74) *Attorney, Agent, or Firm* — Lucas & Mercanti, LLP

(57) ABSTRACT

The present invention relates to a herbal mixture extract of Rehmanniae Radix Preparata and Acanthopanacis Cortex and a composition comprising the same for the prevention and treatment of osteoporosis.
The herbal mixture extract of the present invention enhances the expression of osteoprotegerin (OPG) in osteoblasts and effectively inhibits the generation and activation of osteoclasts, so that it can be effectively used for the prevention and treatment of osteoporosis.

17 Claims, 2 Drawing Sheets

HERBAL MIXTURE EXTRACT OF REHMANNIAE RADIX PREPARATA AND ACANTHOPANACIS CORTEX AND A COMPOSITION COMPRISING THE SAME FOR PREVENTION AND TREATMENT OF OSTEOPOROSIS

CROSS-REFERENCE TO RELATED APPLICATION

This patent application is a Divisional of U.S. patent application Ser. No. 11/844,237, filed on Aug. 23, 2007 now U.S. Pat. No. 8,053,001, which is a continuation of PCT Application Serial No. PCT/KR2006/000634 filed on Feb. 23, 2006, which claims the benefit of priority from Korean Patent Application No. 10-2005-0015049, filed on Feb. 23, 2005, the contents of each of which are incorporated herein by reference.

TECHNICAL FIELD

The present invention relates to a herbal mixture extract of Rehmanniae Radix Preparata and Acanthopanacis Cortex and a composition containing the same as an effective ingredient for the prevention and treatment of osteoporosis.

BACKGROUND ART

Bone is calcified connective tissue joined to muscle, which has hard and thick calcified surface, carries out the function of supporting body by keeping balance and protects organs. The inner bone marrow is myeloid tissue playing a key role in calcium metabolism. Bone is composed of organic substances such as collagen, osteocalcin and osteonectin, inorganic substances such as calcium, phosphorus and fluorine and water. Bone formation and bone resorption are necessary daily processes in vivo. Bone formation is stimulated by low dose of parathyroid hormone, androgen, estrogen, fluorine, phosphorus, etc and bone resorption is stimulated by physical decompression, agravity, a high dose of parathyroid hormone and adrenocortical steroid, etc. Thus, bone metabolism is regulated by the balance between bone formation and bone resorption.

Osteoporosis is caused by unbalance between bone formation and bone resorption. Precisely, osteoporosis progresses when bone resorption outpaces bone formation. With osteoporosis, calcified bone tissue density decreases and thus compact substance of bone is lost gradually, leading to the expansion of marrow cavity. As symptoms progress, which means bone loss is increasing, fracture occurs frequently even with a minimum impulse. Bone tissue is a dynamic tissue which is designed to carry out repeatedly bone formation by osteoblasts and destroy and bone resorption by osteoclasts.

Bone resorption is processed by osteoclasts and a receptor activator of NF-B receptor (RANKL) is essential for the generation and activation of osteoclasts. RANKL exists in osteoblasts and mesenchymal cells and is bound to a receptor activator of NF-B receptor (RANK) [Hofbauer L. C., Khosla S., Dunstan C. R., Lacey D. L., Boyle W. J., Riggs B. L., The roles of osteoprotegerin and osteoprotegerin ligand in the paracrine regulation of bone resorption. *J Bone Miner Res.,* 15(1):2-12, 2000]. Osteoprotegerin (OPG), produced in osteoblasts, acts as a decoy receptor of RANKL to intercept the binding of RANKL and RANK, resulting in the inhibition of differentiation of osteoclast precursors into osteoclasts and activation of osteoclasts [Kong Y. Y., Feige U., Sarosi I., Bolon B., Tafuri A., Morony S., Capparelli C., Li J., Elliott R., McCabe S., Wong T., Campagnuolo G., Moran E., Bogoch E. R., Van G., Nguyen L. T., Ohashi P. S., Lacey D. L., Fish E., Boyle W. J., Penninger J. M.: Activated T cells regulate bone loss and joint destruction in adjuvant arthritis through osteoprotegerin ligand. *Nature,* 402:304-309, 1999; Suda T., Takahashi N., Udagawa N., Jimi E., Gillespie M. T., Martin T. J.: Modulation of osteoclast differentiation and function by the new members of the tumor necrosis factor receptor and ligand families. *Endocr Rev,* 20(3):345-357, 1999; Aubin J. E., Bonnelye E.: Osteoprotegerin and its ligand: a new paradigm for regulation of osteoclastogenesis and bone resorption., *Osteoporos Int,* 11(11):905-913, 2000].

Osteoporosis is divided into primary and secondary types; primary osteoporosis is exemplified by senile osteoporosis and postmenopausal osteoporosis, and secondary osteoporosis is developed as a complication of hyperthyroidism, hyperparathyroidism, hyperadrenocorticism, pregnancy, prolonged fixation (for example, plaster cast fixation), malnutrition, drugs, cancer or other chronic diseases.

The cause of primary osteoporosis has not been disclosed, yet various factors seem to be involved. It is assumed that osteoporosis is developed by unbalance of bone metabolism by aging, calcium deficiency, excessive parathyroid hormone, calcitonin deficiency, active vitamin D deficiency, estrogen deficiency, insufficient exercise, etc. Factors affecting calcium metabolism are parathyroid hormone (PTH), calcitonin (CT) and 1,25-$(OH)_2D_3$, etc. Parathyroid hormone involved in calcium metabolism counteracts calcitonin secreted in C-cells, parafollicular cells of thyroid gland. As a polypeptide, calcitonin having a molecular weight of 3,500-4,000 mediates the deposition of calcium salts in bone. That is, calcitonin reduces blood calcium and magnesium, and phosphate and hydroxyproline in urine. Parathyroid hormone (PTH) is also a polypeptide having molecular weight of 8447. Parathyroid hormone activates osteoclasts, resulting in the increase of bone resorption and activity of vitamin $D_3$ in small intestinal mucosa. So, PTH increases blood calcium and magnesium, and hydroxyproline and phosphate ($PO_4^{3-}$) in urine. Estradiol, asteroid secreted in ovary, activates osteoblasts in bone, thereby inhibits bone resorption.

Postmenopausal women exhibit lower level of estrogen, and as a result, the level of blood calcitonin as well as 1,25-$(OH)_2D_3$ synthesis in kidney is reduced, while the level of PTH is elevated. Accordingly, productions of interleukin 6 (IL-6) and prostaglandin are promoted, resulting in the decrease of calcium absorption in small intestine and the increase of bone loss by active osteoclast mediated bone resorption. As a result, osteoporosis is developed. In general, when bone resorption outpaces bone formation, joint dysfunction, gradual vertebral malformation, minor fracture in vertebra and other regions, lowered mobility by pain (in particular lumbo-dorsal pain) and contracted kidney by kyphosis are observed.

Osteoporosis is characterized more by bone decrease in amount leading to fractures including femur fracture or vertebral fracture than by its symptoms, and has been a public health problem limiting public activities for long-term. So, 15% of causes of death of the aged are attributed to osteoporosis. Bone density is affected by genetic factors, nutrition, hormone changes, exercise and habits. Aging, insufficient exercise, low weight, smoking, low calcium diet, menopause and ovariectomy are known as major causes of osteoporosis.

In the meantime, it is known that black people exhibit lower bone resorption level than white people, meaning black people have bigger bone mass. The peak bone mass is observed between age 14 and 18, and then reduces 1% per year. In particular, bone is continuously decreased from the age of 30 in women, and is rapidly reduced after menopause by hormone change.

Osteoporosis, more or less, is inevitable in the aged, especially in postmenopausal women, so osteoporosis and its therapeutic agent have been in the center of our concern as an aging population grows in advanced countries.

The treatment of bone diseases forms approximately 130 billion dollar-market throughout the world, which is assumed to be growing further. Thus, numbers of research teams and pharmaceutical companies have invested to develop a therapeutic agent for bone diseases and an inhibitor for bone resorption.

Osteoporosis-related studies have been focused on inorganic substances in bone, specifically on calcium and phosphorus metabolism, so far. However, concrete pathogenic mechanism has not been disclosed, yet.

A therapeutic agent for osteoporosis being used today is exemplified by bisphosphonate products (alendronate, etidronate), hormone products (raloxifene), vitamin D products, calcitonin products and calcium products, etc. However, bisphosphonate products have problems of low absorption rate, troublesome administration methods and inducing esophagitis. Hormone products require life-time administration, which has possibility of carrying side effects such as breast cancer, uterine cancer, cholelithiasis and thrombosis, etc. Vitamin D products are expensive but not much effective. Calcitonin products have also problems of high costs and hard administration. Calcium products have less side effects but are limited to rather prevention than treatment.

Short-term administration of a drug is not much effective for the treatment of osteoporosis, and thus long-term administration of a drug is inevitable. Therefore, a novel agent having less side effects but more medicinal effects is required for long-term administration.

The present inventors, thus, have studied on various physiological activities of Rehmanniae Radix Preparata and Acanthopanacis Cortex. And the inventors finally completed the present invention by confirming that a herbal mixture extract of Rehmanniae Radix Preparata and Acanthopanacis Cortex has no toxicity, enhances the expression of osteoprotegerin, a protein inhibiting generation and activation of osteoclasts, and suppresses osteoclast proliferation, so that the mixture can be effectively used for the prevention and treatment of osteoporosis.

DISCLOSURE

Technical Problem

It is an object of the present invention to provide a herbal mixture extract of Rehmanniae Radix Preparata and Acanthopanacis Cortex having activities of promoting the expression of osteoprotegerin (OPG) in osteoblasts and inhibiting the generation of osteoclasts.

It is another object of the present invention to provide a composition for the prevention and treatment of osteoporosis containing the herbal mixture extract as an effective ingredient.

Technical Solution

To achieve the above object, the present invention provides a herbal mixture extract of Rehmanniae Radix Preparata and Acanthopanacis Cortex having activities of promoting the expression of osteoprotegerin (OPG) in osteoblasts and inhibiting the generation of osteoclasts.

Also, the present invention provides a composition for the prevention and treatment of osteoporosis containing the herbal mixture extract as an effective ingredient.

DESCRIPTION OF DRAWINGS

The application of the preferred embodiments of the present invention is best understood with reference to the accompanying drawings, wherein.

BEST MODE

Figure 1:
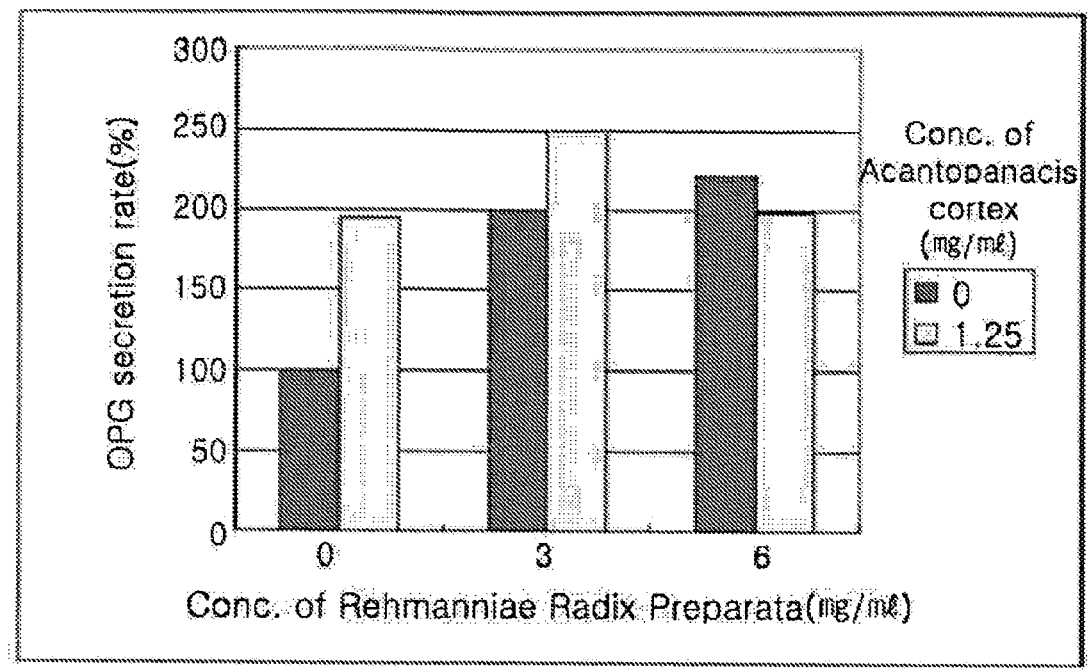
FIG. 1 is a graph showing the expression of OPG in an osteoblast cell line MG63 treated with the herbal mixture extract according to an embodiment example of the present invention detected by ELISA.

Hereafter, the present invention is described in detail.

The present invention provides a herbal mixture extract of Rehmanniae Radix Preparata and Acanthopanacis Cortex having activities of promoting the expression of osteoprotegerin (OPG) in osteoblasts and inhibiting the generation of osteoclasts.

Rehmanniae Radix Preparata is a root of a medicinal plant belonging to Scrophulariaceae, which has been used as a traditional oriental medicine after being steamed and dried. The raw Rehmanniae Radix Preparata is called Rehmanniae radix crudus Libosch, and the dried Rehmanniae Radix Preparata is called Rehmanniae Radix Libosch. In particular, the one which has been through steam-dry processes after being dipped in alcohol nine times is called 'Gujihwang', whose medicinal effect is known as the best. It has sweet and bitter taste at the same time and has property of making things warm, by which it can supplement blood and energy (a basic substance necessary for the life and vital activity) so that it helps the treatment of the coldness of knees and lower back and menstrual irregularity, in addition to making hair black and healthy. Rehmanniae Radix Preparata is one of major components for Samultang and has been administered for relieving fever, dried throat and dipsesis, symptoms of being weak. Besides, it has been known in folk remedies that Rehmanniae Radix Preparata shows therapeutic effect on constipation when it is administered together with pork soup.

Acanthopanacis Cortex is a shrub belonging to Araliaceae, which is only found in far-east Asia in northern hemisphere. In particular, Acanthopanacis Cortex is classified as a reserved wild plant in South Korea, which is on the brink of extinction. Acanthopanacis Cortex is divided into *Acanthopanax senticosus, Acanthopanax* and *Acanthopanax koreanum*. The roots and barks of Acanthopanacis cortex have been used as top-ranked medicine since they have not shown any toxicity or side effects so far. The leaf of Acanthopanacis cortex contains chilsanoside, which has pharmaceutical effect. The roots of Acanthopanacis Cortex contain not only Acanthopanacis Cortex glycoside but also syringin and coumarin glycosides. Acanthopanacis Cortex contains acanthosides B and D, which are Acanthopanacis Cortex glycosides, and water-soluble polysaccharides enhancing immunity. Its' taste is bitter and hot and it has a property of warming things up. It is known to eliminate gout in liver and nervous systems, invigorate and bring essence in a body. It has been prescribed for such diseases as Oro (fatigue caused by the weakness of five internal organs), Chilsang (seven representative symptoms shown in men caused by the weakness of a body) and difficulty in moving legs. Long-term administration of Acanthopanacis Cortex increases energy, protects the stomach, invigorates, clears mind, increases will power, prevents aging, helps having a light heart and clear the blood in a body. So, Acanthopanacis Cortex has been used for the treatment of such symptoms as pain in backbone, male impotence, scrotal eczema, female amenorrhea, etc.

The herbal mixture extract of Rehmanniae Radix Preparata and Acanthopanacis Cortex of the present invention is extracted using mixed solution of Rehmanniae Radix Preparata and Acanthopanacis Cortex with water, $C_1 \sim C_4$ alcohol or the mixture of water and $C_1 \sim C_4$ alcohol, and more preferably using water. The herbal mixture extract is prepared as follows.

Rehmanniae Radix Preparata and Acanthopanacis Cortex are washed thoroughly with water and dried in the shadow. They are put in an extraction vessel, to which a solvent is added, followed by extraction. The extract is cooled down at room temperature, followed by filtering with a filter paper. Then, the extract is concentrated under reduced pressure by using vacuum rotation evaporator, followed by freeze-drying. As a result, powder type Rehmanniae Radix Preparata and Acanthopanacis Cortex extracts are respectively prepared. The two extracts of Rehmanniae Radix Preparata and Acanthopanacis Cortex are mixed to prepare a herbal mixture extract.

Extraction can be performed by the conventional methods such as maceration, infusion and heat extraction by using a proper solvent, and in particular hot water extraction at 100° C. for 4 hours is preferred.

And, it is preferred for the herbal mixture extract that Rehmanniae Radix Preparata extract and Acanthopanacis Cortex extract are mixed at the weight ratio of 15.0:0.5~0.15: 5.0, and is more preferred to be mixed at the ratio of 8:1~1:4. It is most preferred to mix Rehmanniae Radix Preparata extract and Acanthopanacis Cortex extract at the weight ratio of 4:1~1:1.

The herbal mixture extract of the present invention enhances the expression of osteoprotegerin which inhibits the generation and activation of osteoclasts (FIG. 1).

Figure 2:
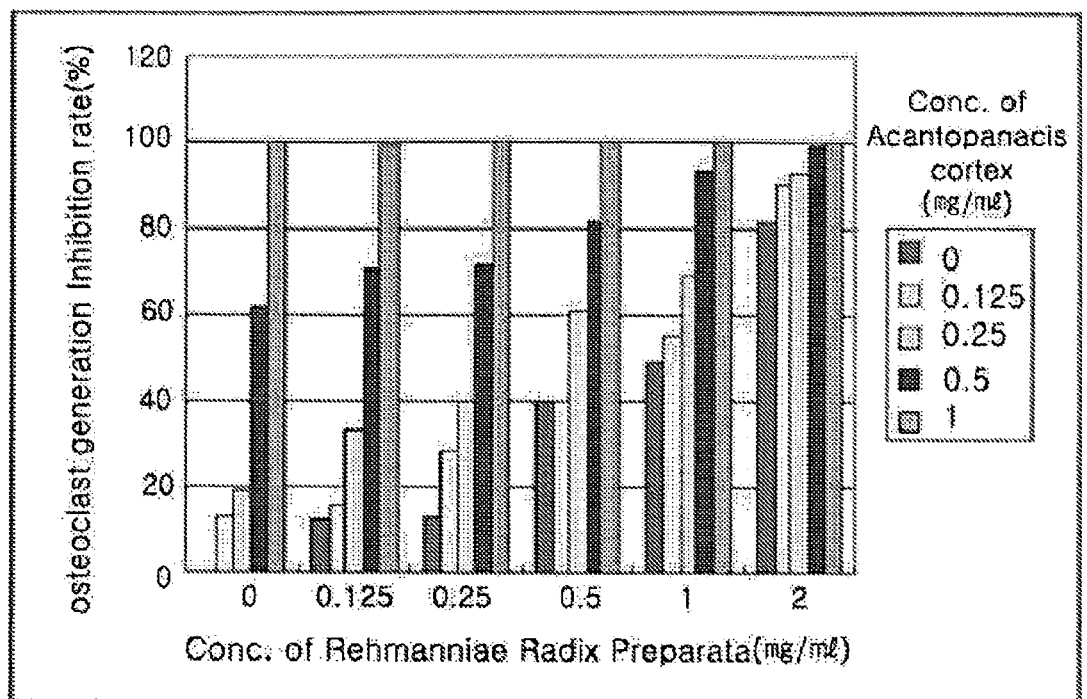
FIG. 2 is a graph showing the inhibition of osteoclast generation by the herbal mixture extract according to an embodiment example of the present invention.

The herbal mixture extract of the present invention has an effect of inhibiting the generation of osteoclasts (FIG. 2).

The outstanding promoting effect on the expression of osteoprotegerin in osteoblasts and inhibiting effect on the generation of osteoclasts are observed when the herbal mixture extract of Rehmanniae Radix Preparata extract and Acanthopanacis Cortex is prepared at the weight ratio of 8:1~1:4 and more preferably at the weight ratio of 4:1~1:1. When the two components are mixed together, the above effects are greater than when each extract is used independently.

The herbal mixture extract of the present invention has activities of enhancing the expression of osteoprotegerin inhibiting the generation and activation of osteoclasts and suppressing the generation of osteoclasts, so that it can be effectively used as a composition for the prevention and treatment of osteoporosis.

The herbal mixture extract of the present invention was orally administered to rats to investigate toxicity. As a result, it was evaluated to be safe substance since its estimated $LD_{50}$ value (50% lethal dose) is much greater than 1 g/kg in rats.

The present invention also provides a composition for the prevention and treatment of osteoporosis containing the above herbal mixture extract as an effective ingredient.

The composition of the present invention can additionally include, in addition to the herbal mixture extract, one or more effective ingredients having the same or similar functions to the extract of the invention.

The herbal mixture extract of the present invention can be administered orally or parenterally and be used in general forms of pharmaceutical formulation.

The herbal mixture extract of the present invention can be prepared for oral or parenteral administration by mixing with generally used fillers, extenders, binders, wetting agents, disintegrating agents, diluents such as surfactant, or excipients. Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used. Liquid formulations for oral administrations are suspensions, solutions, emulsions and syrups, and the abovementioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester ethylolate, etc. Suppositories can contain, in addition to the active compound or compounds, witepsol, macrogol, tween 61, cacao butter, laurin butter, glycerogelatin, etc. In addition, calcium or vitamin $D_3$ can be included to enhance the preparative or therapeutic effect on osteoporosis.

The effective dosage of the composition can be determined according to weight, age, gender, health condition, diet, administration frequency, administration method, excretion and severity of a disease. The dosage of the composition is 1~1000 mg/kg per day, and preferably 300~700 mg/kg per day. More preferably, the dosage is 150~450 mg/kg per day. Administration frequency is 1~6 times a day.

The composition of the present invention can be administered singly or treated along with surgical operation, hormone therapy, chemotherapy and biological reaction regulator, to prevent and treat osteoporosis.

The composition of the present invention can be included in health food for the purpose of alleviating symptoms of osteoporosis. At this time, the herbal mixture extract of the present invention can be added as it is or after being mixed with other food or ingredients, according to the conventional method. The mixing ratio of effective ingredients is determined by the purpose of use (prevention, health or therapeutic treatment).

There is no limit in applicable food, which is exemplified by meats, sausages, bread, chocolate, candies, snacks, cookies, pizza, ramyun, noodles, dairy products including ice cream, soups, beverages, tea, drinks, alcoholic drinks and vitamin complex, etc, and in fact every health food generally produced are all included.

Health beverages containing the composition of the present invention can additionally include various flavors or natural carbohydrates, etc, like other beverages. The natural carbohydrates above can be one of monosaccharide such as glucose and fructose, disaccharides such as maltose and sucrose, polysaccharides such as dextrin and cyclodextrin, and sugar alcohols such as xylitol, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01~0.04 g to 100 ml, more preferably 0.02~0.03 g to 100 ml.

In addition to the ingredients mentioned above, the composition of the present invention can include in variety of nutrients, vitamins, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01~0.1 weight part per 100 weight part of the composition of the invention.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Herbal Extracts

Cultivated Rehmanniae Radix Preparata and Acanthopanacis Cortex were purchased from a wholesale dried medicinal herb store.

<1-1> Preparation of Rehmanniae Radix Preparata Extract

Rehmanniae Radix Preparata was washed with clean water and dried in the shadow. 100 g of the dried Rehmanniae Radix Preparata was put in a 3 l extraction vessel, to which 1 l of distilled water was added, followed by hot water extraction for 4 hours at 100□. The process was repeated three times, and the resultant solution was cooled down at room temperature, followed by filtering with a filter paper. The extracted solution was concentrated under reduced pressure under 40° C. by using vacuum rotary evaporator. As a result, Rehmanniae Radix Preparata extract was obtained (yield: 42%).

<1-2> Preparation of Acanthopanacis Cortex Extract

Acanthopanacis Cortex was washed with clean water and dried in the shadow. 100 g of the dried Acanthopanacis Cortex was put in a 3 l extraction vessel, to which 1 l of distilled water was added, followed by hot water extraction for 4 hours at 100□. The process was repeated three times, and the resultant solution was cooled down at room temperature, followed by filtering with a filter paper. The extracted solution was concentrated under reduced pressure under 40° C. by using vacuum rotary evaporator, followed by freeze-drying. As a result, powder extract of Acanthopanacis Cortex was obtained (yield: 5.8%).

<1-3> Preparation of Herbal Mixture Extract 0.15~15.0 weight part of Rehmanniae Radix Preparata extract obtained in Example 1-1 and 0.5~5.0 weight part of Acanthopanacis Cortex extract obtained in Example <1-2> were mixed at a proper ratio, and the herbal mixture extract was diluted in cell culture medium to be used for further experiments.

Experimental Example 1

Effect of Herbal Mixture Extract of the Present Invention on the Expression of Osteoprotegerin in Osteoblasts Following experiments were performed to investigate the effect of herbal mixture extract of the present invention on the expression of osteoprotegerin in osteoblasts.

<1-1> Culture of Osteoblasts

To evaluate the effect of the herbal mixture extract of the invention on the expression of osteoprotegerin in osteoblasts, human osteosarcoma cell lines MG-63 and HOS were purchased from ATCC (American Type Culture Collection, Rockville, USA). The cells were cultured in DMEM (Dulbecco's modified Eagle's medium) supplemented with 10% fetal bovine serum (FBS) in a 37° C. $CO_2$ incubator with 95% humidity.

<1-2> Measurement of the Expression of Osteoprotegerin Inhibiting the Generation of Osteoclasts The present inventors investigated whether the level of OPG was increased by treating the extract obtained in Example 1 to the culture of osteoblasts.

MG-63 cells, prepared in the above Experimental Example <1-1>, were cultured in a 96-well plate until confluented. The plate was treated with 2 ml of serum free DMEM containing the herbal mixture extract with various concentrations, followed by further culturing for 16 hours. Supernatant was obtained. The level of OPG was measured by ELISA. Optocal density (O.D.) was measured by using Dynatech MR-7000 (Dynatech Laboratorie) at 450 nm and the amount of secreted OPG was calculated by percentage for control treated only with medium according to the below Mathematical Formula 1.

$$\text{Increase rate of } OPG \text{ release } (\%) = (1 - O.D._{450} \text{ of experimental group}/O.D._{450} \text{ of control group})100 \qquad \text{<Mathematical Formula 1>}$$

(In the Formula, $O.D._{450}$ means optical density at 450 nm)

As shown in Table 1, treatment of Rehmanniae Radix Preparata extract of the <example 1> with 3 and 6 mg/ml increased the expression of OPG, a protein inhibiting the generation of osteoclasts, 200% and 221% respectively, and treatment of Acanthopanacis Cortex extract with 1.25 mg/ml also increased the expression of OPG upto 194%, suggesting that two single herbal extracts increase OPG expression dose-dependently. In the meantime, when the herbal extracts were used as a mixture, OPG level was 120~130% increased (Table 1, FIG. 1). OPG expression inducing effect of the herbal mixture extract was remarkably enhanced when Rehmanniae Radix Preparata extract and Acanthopanacis Cortex extract were mixed with 3 mg/ml and 1.25 mg/ml respectively, compared with when Rehmanniae Radix Preparata extract was added by 6 mg/ml. The above results indicate that the mixing ratio of Rehmanniae Radix Preparata extract and Acanthopanacis Cortex extract in the preparation of a herbal mixture is important to enhance OPG expression.

TABLE 1

| | OPG secretion rate (%) | | |
|---|---|---|---|
| | | *Acanthopanacis Cortex* extract | |
| | Conc. (mg/ml) | 0 | 1.25 |
| *Rehmanniae Radix Preparata* extract | 0 | 0 | 194.8 |
| | 3 | 200.4 | 249.2 |
| | 6 | 221.6 | 198.2 |

From the above results, it was confirmed that the herbal mixture extract of the present invention increases the expression of OPG, a protein inhibiting the generation of osteoclasts, and thereby inhibits the generation of osteoclasts.

Experimental Example 2

Osteoclast Generation Inhibitory Activity of Herbal Mixture Extract of the Present Invention To examine the effect of herbal mixture extract of the present invention on the generation and activity of osteoclasts, osteoclast precursor cells were cultured in a calcium-phosphate coated plate (OAAS, Oscotec Inc.), followed by investigation of the activity of TRAP (tartrate-resistant acid phosphatase), an osteoclast marker.

<2-1> Isolation of Osteoclast Precursor Cells and Differentiation of Osteoclast Precursor Cells into Mature Osteoclasts To isolate mouse bone marrow cells, male mouse at 7-9 weeks old was sacrificed by cervical dislocation, then femur and tibia were extracted under aseptic condition. Soft tissue was removed and both ends of bone were cut out. 1 ml of an enzyme solution containing 0.1% collagenase (Gibco), 0.05% trypsin and 0.5 mM EDTA (Gibco) was flushed into one end of marrow cavity by using 26 G needle. Bone marrow was taken out, followed by stirring for 30 minutes. Bone marrow cells were recovered and pre-cultured for 24 hours in α-MEM (α-minimum essential medium) supplemented with 10% FBS. Unattached cells were obtained. The unattached cells, osteoclast precursor cells, were seeded into a plate ($2 \times 10^5$ cells per well), followed by culture. The herbal mixture extract of the invention was treated to α-MEM containing 20 ng/ml of macrophage-colony stimulating factor (M-CSF, Peprotech, USA) and 30 ng/ml of RANKL (Peprotech, USA) during the 8-day of culture. Upon completion of the culture, cells were fixed and TRAP staining was performed to examine the generation of osteoclasts.

<2-2> Formation of Trap(+) Multinucleated Cells (MNCs)

To examine the generation of osteoclasts, osteoclast precursor cells were cultured in calcium-phosphate coated plate and then TRAP(+) MNCs were counted.

Particularly, upon completion of cell culture, attached cells were washed with PBS and fixed with citrate-acetate-formaldehyde for 5 minutes. The cells were further cultured in 37° C. acetate buffer (pH5.0) containing naphthol AS-BI phosphate, fast Garnet GBC solution and 7 mM tartrate buffer (pH 5) for one hour, followed by staining with TRAP. TRAP(+) MNCs having more than 3 nuclei were considered as osteoclasts. The herbal mixture extract prepared in Example 1 and each single extract were treated to the cells. After 8 days of culture, TRAP(+) MNCs were counted again and osteoclast generation inhibiting rate was calculated thereby according to the below Mathematical Formula 2.

TRAP(+) MNCs gengration inhibition rate (%)=100−(Number of TRAP(+) MNCs of experimental group/Number of TRAP(+) MNCs of control group)×100  <Mathematical Formula 2>

TABLE 2

| | Osteoclast generation inhibition rate (%) | | | | | |
|---|---|---|---|---|---|---|
| | | Acanthopanacis Cortex extract | | | | |
| | Conc. (mg/ml) | 0 | 0.125 | 0.25 | 0.5 | 1 |
| Rehmanniae | 0 | 0.00 | 12.77 | 19.28 | 61.61 | 99.74 |
| Radix | 0.125 | 12.43 | 15.85 | 33.42 | 70.69 | 99.57 |
| Preparata | 0.25 | 12.68 | 28.19 | 40.10 | 71.64 | 99.83 |
| extract | 0.5 | 40.10 | 40.02 | 60.84 | 81.92 | 100.00 |
| | 1 | 49.01 | 55.01 | 68.98 | 93.32 | 100.00 |
| | 2 | 81.75 | 90.15 | 92.89 | 99.31 | 100.00 |

As shown in Table 2 and FIG. 2, osteoclast generation inhibiting rate of control group treated no extract was considered 0, and based on that, osteoclast generation inhibiting rates of each experimental group treated with different extracts with different concentrations were compared. The TRAP(+) MNCs generation inhibition rates were 12.43, 12.68, 40.10, 49.01 and 81.75% at the concentration of 0.125, 0.25, 0.5, 1 and 2 mg/ml, respectively, when Rehmanniae Radix Preparata extract was independently treated. In the meantime, when Acanthopanacis Cortex extract was independently treated, the generation and activation of osteoclasts were inhibited 12.77, 19.28, 61.61 and 99.74% at the concentration of 0.125, 0.25, 0.5 and 1 mg/ml respectively, suggesting that the independent treatment of each herbal extract inhibited TRAP(+) MNCs generation dose-dependently.

While Rehmanniae Radix Preparata extract showed no more than 50% inhibiting effect at the concentration of upto 0.5 mg/ml, or even with increasing the concentration, the co-treatment of Rehmanniae Radix Preparata extract with Acanthopanacis Cortex extract displayed 100% inhibiting effect even at low concentration. The formation of osteoclasts was remarkably inhibited when Rehmanniae Radix Preparata extract and Acanthopanacis Cortex extract were mixed with more than 0.25 mg/ml each, in particular when Rehmanniae Radix Preparata extract was included more than 20 weight % and Acanthopanacis Cortex extract was included more than 10 weight %, more preferably when Rehmanniae Radix Preparata extract was included more than 50 weight % and Acanthopanacis Cortex extract was included more than 25 weight %. When the contents of those extracts were less than the above range, osteoclast generation was not that much inhibited.

Therefore, it was confirmed that the herbal mixture extract of the present invention inhibits the generation and activation of osteoclasts better than each independent herbal extract, Rehmanniae Radix Preparata extract and Acanthopanacis Cortex extract, can do.

EXPERIMENTAL EXAMPLE 3

Acute Toxicity in Rats Tested Via Oral Administration

The following experiments were performed to see if the herbal mixture extracts of the present invention have acute toxicity in rats.

6-week old specific pathogen-free (SPF) SD rats were used in the tests for acute toxicity. The herbal mixture extract of the present invention was suspended in 0.5% methylcellulose solution and orally administered once to 2 rats per group at the dosage of 1 g/kg/ml. Death, clinical symptoms and weight change in mice were observed, hematological tests and biochemical tests of blood were performed, and any abnormal signs in the gastrointestinal organs of chest and abdomen were checked with eyes during autopsy.

The results showed that the herbal mixture extract of the present invention did not cause any specific clinical symptoms, weight change or death in rats. No change was observed in hematological tests, biochemical tests of blood and autopsy.

Therefore, the herbal mixture extract used in this experiment was evaluated to be safe substance since it did not cause any toxic change in rats up to the level of 1 g/kg and its estimated $LD_{50}$ values are much greater than 1 g/kg in mice.

The Manufacturing Examples of the composition for the present invention are described hereinafter.

Manufacturing Example 1

Preparation of Pharmaceutical Formulations

<1-1> Preparation of Powders

| Herbal mixture extract of the present invention | 2 g |
| --- | --- |
| Lactose | 1 g |

Powders were prepared by mixing all the above components and filled airtight bag with them.

<1-2> Preparation of Tablets

| Herbal mixture extract of the present invention | 100 mg |
| --- | --- |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| Herbal mixture extract of the present invention | 100 mg |
| --- | --- |
| Corn starch | 100 mg |
| Lactose | 100 mg |
| Magnesium stearate | 2 mg |

Capsules were prepared by mixing the components above and filled gelatin capsules with them according to the conventional method for capsules.

Manufacturing Example 2

Preparation of Food

Foodstuff containing the herbal mixture extract of the present invention was prepared as follows.
<2-1> Preparation of Flour Food
Health improving flour food was prepared by adding the herbal mixture extract of the present invention by 0.5~5.0 weight % to wheat flour and then making the flour into bread, cakes, cookies, crackers and noodles.
<2-2> Preparation of Dairy Products
The herbal mixture extract of the present invention was added by 5~10 weight % to milk to prepare health improving dairy products such as butter, ice cream, etc.
<2-3> Preparation of Sunsik
Brown rice, barley, glutinous rice and *coix* (job's tear) were gelatinized by the conventional method, followed by drying. The dried mixture was distributed and pulverized, resulting in 60-mesh size grain powders.

Black bean, black sesame and *perilla* were steamed and dried by the conventional method. The dried mixture was distributed and pulverized, resulting in 60-mesh size grain powders.

The herbal mixture extract of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and dried herbal mixture extract powders were all mixed at the following ratio.

Grain (brown rice 30 weight %, *coix* 15 weight %, barley 20 weight %), Seeds (*perilla* 7 weight %, black bean 8 weight %, black sesame 7 weight %),
Dried powder of herbal mixture extract (3 weight %),
*Ganoderma lucidum* (0.5 weight %),
*Rehmannia glutinosa* (0.5 weight %)

Manufacturing Example 3

Preparation of Beverages

<3-1> Preparation of Carbonated Beverages
Sugar (5~10%), citric acid (0.05~0.3%), caramel (0.005~0.02%) and vitamin C (0.1~1%) were mixed, to which purified water (79~94%) was added to make syrup. The prepared syrup was sterilized at 85~98° C. for 20~180 seconds, then mixed with cooling water at the ratio of 1:4. Then, carbon dioxide gas (0.5~0.82%) was given to the mixture to prepare carbonated beverages containing the herbal mixture extract of the present invention.
<3-2> Preparation of Health Beverages
Acid fructose (0.5%), oligosaccharide (2%), sugar (2%), salt (0.5%) and water (75%) were all mixed with the herbal mixture extract of the present invention evenly, followed by sterilization. The mixture was put in a small container such as a glass bottle or pat bottle, resulting in health beverages.
<3-3> Preparation of Vegetable Juice
5 g of the herbal mixture extract of the present invention was added to 1,000 ml of tomato or carrot juice to prepare health vegetable juice.
<3-4> Preparation of Fruit Juice
1 g of the herbal mixture extract of the present invention was added 1,000 ml of apple or grape juice to produce health fruit juice.

INDUSTRIAL APPLICABILITY

As described hereinbefore, the herbal mixture extract of Rehmanniae Radix Preparata and Acanthopanacis Cortex of the present invention has effects of inhibiting the generation and activation of osteoclasts by enhancing the expression of osteoprotegerin in osteoblasts and inhibiting the generation of osteoclasts, thereby. In particular, when the mixture contains Rehmanniae Radix Preparata extract more than 20 weight % and Acanthopanacis Cortex extract more than 10 weight %, more preferably when the mixture contains Rehmanniae Radix Preparata extract more than 50 weight % and Acanthopanacis Cortex extract more than 25 weight %, the inhibiting effects were remarkably enhanced, compared with when each extract was treated independently. Thus, the herbal mixture extract of the invention, owing to its synergy effect, can effectively used for the prevention and treatment of osteoporosis as medicinal agent and health food.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating osteoporosis in a subject in need thereof comprising administering to the subject a therapeutically effective amount of an herbal extract mixture consisting of an extract of Rehmanniae Radix Preparata and an extract of Acanthopanacis Cortex, wherein the extract of Rehmanniae Radix Preparata and the extract of Acanthopanacis Cortex are mixed at the weight ratio of 16:1~1:4.

2. The method as set forth in claim 1, wherein the extract of Rehmanniae Radix Preparata and the extract of Acanthopanacis Cortex are mixed at the weight ratio of 8:1~1:4.

3. The method as set forth in claim 1, wherein the extract of Rehmanniae Radix Preparata and the extract of Acanthopanacis Cortex are mixed at the weight ratio of 4:1~1:1.

4. The method as set forth in claim 1, wherein the extract of Rehmanniae Radix Preparata is prepared by extracting Rehmanniae Radix Preparata with water, $C_1$~$C_4$ alcohol or their mixture and the extract of Acanthopanacis Cortex is prepared by extracting Acanthopanacis Cortex with water, $C_1$~$C_4$ alcohol or their mixture.

5. The method as set forth in claim 1, wherein the extract of Rehmanniae Radix Preparata is prepared by extracting Rehmanniae Radix Preparata with water and the extract of Acanthopanacis Cortex is prepared by extracting Acanthopanacis Cortex with water.

6. A method for accelerating osteoprotegerin (OPG) expression in osteoblasts in a subject in need thereof comprising administering to the subject a therapeutically effective amount of an herbal extract mixture consisting of an extract of Rehmanniae Radix Preparata and an extract of Acanthopanacis Cortex, wherein the extract of Rehmanniae Radix Preparata and the extract of Acanthopanacis Cortex are mixed at the weight ratio of 16:1~1:4.

7. The method as set forth in claim 6, wherein the extract of Rehmanniae Radix Preparata and the extract of Acanthopanacis Cortex are mixed at the weight ratio of 8:1~1:4.

8. The method as set forth in claim 6, wherein the extract of Rehmanniae Radix Preparata and the extract of Acanthopanacis Cortex are mixed at the weight ratio of 4:1~1:1.

9. The method as set forth in claim 6, wherein the extract of Rehmanniae Radix Preparata is prepared by extracting Rehmanniae Radix Preparata with water, $C_1$~$C_4$ alcohol or their mixture and the extract of Acanthopanacis Cortex is prepared by extracting Acanthopanacis Cortex with water, $C_1$~$C_4$ alcohol or their mixture.

10. The method as set forth in claim 6, wherein the extract of Rehmanniae Radix Preparata is prepared by extracting Rehmanniae Radix Preparata with water and the extract of Acanthopanacis Cortex is prepared by extracting Acanthopanacis Cortex with water.

11. A method for inhibiting osteoclast generation in a subject in need thereof comprising administering to the subject a therapeutically effective amount of an herbal extract mixture consisting of an extract of Rehmanniae Radix Preparata and an extract of Acanthopanacis Cortex, wherein the extract of Rehmanniae Radix Preparata and the extract of Acanthopanacis Cortex are mixed at the weight ratio of 16:1~1:4.

12. The method as set forth in claim 11, wherein the extract of Rehmanniae Radix Preparata and the extract of Acanthopanacis Cortex are mixed at the weight ratio of 8:1~1:4.

13. The method as set forth in claim 11, wherein the extract of Rehmanniae Radix Preparata and the extract of Acanthopanacis Cortex are mixed at the weight ratio of 4:1~1:1.

14. The method as set forth in claim 11, wherein the extract of Rehmanniae Radix Preparata is prepared by extracting Rehmanniae Radix Preparata with water, $C_1$~$C_4$ alcohol or their mixture and the extract of Acanthopanacis Cortex is prepared by extracting Acanthopanacis Cortex with water, $C_1$~$C_4$ alcohol or their mixture.

15. The method as set forth in claim 11, wherein the extract of Rehmanniae Radix Preparata is prepared by extracting Rehmanniae Radix Preparata with water and the extract of Acanthopanacis Cortex is prepared by extracting Acanthopanacis Cortex with water.

16. A method for alleviating symptoms of osteoporosis in a subject in need thereof comprising administering to the subject a therapeutically effective amount of an herbal extract mixture consisting of an extract of Rehmanniae Radix Preparata and an extract of Acanthopanacis Cortex, wherein the extract of Rehmanniae Radix Preparata and the extract of Acanthopanacis Cortex are mixed at the weight ratio of 16:1~1:4.

17. The method as set forth in claim 16, wherein the herbal extract mixture is included in health food.

* * * * *